United States Patent
Togaru

(10) Patent No.: US 11,035,812 B2
(45) Date of Patent: Jun. 15, 2021

(54) STRUCTURAL HEALTH MONITORING APPARATUS AND MONITORING METHOD

(71) Applicant: UNEBE CORPORATION, Toyota (JP)

(72) Inventor: Takeshi Togaru, Toyota (JP)

(73) Assignee: UNEBE CORPORATION, Toyota (JP)

( * ) Notice: Subject to any disclaimer, the term of this patent is extended or adjusted under 35 U.S.C. 154(b) by 408 days.

(21) Appl. No.: 15/592,914

(22) Filed: May 11, 2017

(65) Prior Publication Data

US 2017/0269014 A1 Sep. 21, 2017

Related U.S. Application Data

(63) Continuation of application No. PCT/JP2015/079164, filed on Oct. 15, 2015.

(30) Foreign Application Priority Data

Oct. 21, 2014 (JP) .............................. JP2014-214777

(51) Int. Cl.
*G01N 27/04* (2006.01)
*G01N 27/20* (2006.01)
(Continued)

(52) U.S. Cl.
CPC ............. *G01N 27/041* (2013.01); *E04B 1/18* (2013.01); *G01N 27/04* (2013.01); *G01N 27/20* (2013.01);
(Continued)

(58) Field of Classification Search
CPC .................................................. G01N 27/041
See application file for complete search history.

(56) References Cited

U.S. PATENT DOCUMENTS

| 5,952,836 A * | 9/1999 | Haake | G01R 31/58 324/718 |
| 2005/0139001 A1* | 6/2005 | van Schoor | G01M 5/0041 73/159 |

(Continued)

FOREIGN PATENT DOCUMENTS

| EP | 2 063 243 A1 | 5/2009 |
| JP | 2001-242112 | 9/2001 |

(Continued)

OTHER PUBLICATIONS

International Search Report dated Dec. 22, 2015 in PCT/JP2015/079164 filed on Oct. 15, 2015 (with English translation).

(Continued)

*Primary Examiner* — John E Breene
*Assistant Examiner* — Jeffrey C Morgan
(74) *Attorney, Agent, or Firm* — Oblon, McClelland, Maier & Neustadt, L.L.P.

(57) ABSTRACT

According to one embodiment, a structural health monitoring apparatus for monitoring health of a structure includes a resistance measurement unit and an evaluation unit. The resistance measurement unit measures a resistance value between one terminal and another terminal of a set of two terminals. The set of two terminals is selected from a plurality of terminals provided on the electrical paths formed in the assembled body that forms frames of the structure. The evaluation unit evaluates the health of the structure by using a difference between the resistance value between terminals of the set of two terminals and a reference resistance value between the two terminals, and outputs evaluation result information.

13 Claims, 9 Drawing Sheets

(51) Int. Cl.
      *E04B 1/18*       (2006.01)
      *G05B 23/02*     (2006.01)
      *E04B 1/00*       (2006.01)
      *G01N 33/46*     (2006.01)

(52) U.S. Cl.
      CPC ............ *G05B 23/0213* (2013.01); *E04B 1/00* (2013.01); *G01N 33/46* (2013.01)

(56) References Cited

U.S. PATENT DOCUMENTS

| | | | |
|---|---|---|---|
| 2005/0284232 A1* | 12/2005 | Rice | G01N 27/205 73/762 |
| 2007/0118335 A1* | 5/2007 | Andarawis | G01M 5/00 702/188 |
| 2010/0005895 A1 | 1/2010 | Lv et al. | |

FOREIGN PATENT DOCUMENTS

| | | |
|---|---|---|
| JP | 2003-307403 | 10/2003 |
| JP | 2004-69680 | 3/2004 |
| JP | 2007-122175 | 5/2007 |
| JP | 2007-263674 | 10/2007 |
| JP | 2010-230344 | 10/2010 |
| JP | 2011-242135 A | 12/2011 |
| JP | 5793784 | 10/2015 |

OTHER PUBLICATIONS

Extended European Search Report dated Mar. 16, 2018 in European Patent Application No. 15852382.9, 9 pages.

Combined Chinese Office Action and Search Report dated Mar. 1, 2019 in Patent Application No. 201580067494.8 (with English translation of Categories of Cited Documents), 7 pages.

* cited by examiner

| i | SET OF TERMINALS | RESISTANCE VALUE Ri(t) | | | |
|---|---|---|---|---|---|
| | | t1 | t2 | ... | t=t |
| 1 | t l1, t l2 | R1(t1) | R1(t2) | ... | R1(t) |
| 2 | t l3, t l4 | R2(t1) | R2(t2) | ... | R2(t) |
| 3 | t l5, t l6 | R3(t1) | R3(t2) | ... | R3(t) |
| ⋮ | ⋮ | ⋮ | ⋮ | ⋮ | ⋮ |
| m | t l1, t l6 | Rm(t1) | Rm(t2) | ... | Rm(t) |

STRUCTURAL HEALTH MONITORING APPARATUS AND MONITORING METHOD

CROSS-REFERENCE TO RELATED APPLICATIONS

This application is a Continuation Application of No. PCT/JP2015/079164, filed Oct. 15, 2015, and the PCT application is based upon and claims the benefit of priority from Japanese Patent Application No. 2014-214777, filed Oct. 21, 2014, the entire contents of which are incorporated herein by reference.

FIELD

Embodiments described herein relate generally to a structural health monitoring apparatus and a structural health monitoring method for monitoring health of a structure.

BACKGROUND

A structure, such as a steel structure building, a reinforced concrete building, and a wood structure building (wooden building), deteriorates over time and deteriorates due to external factors, such as an earthquake and a fire. Furthermore, biological factors, such as pests and decay, cannot be ignored as causes of deterioration of the wooden building. Appropriate handling (maintenance) according to the causes and the conditions of the deterioration is important in extending the life of the structure.

Meanwhile, some wooden buildings, such as shrines and temples, remain for a long time. One of the reasons that the wooden buildings can remain for a long time is that structural materials (such as columns, beams, and foundations) of structures can be checked with eyes. When the structural materials can be checked with eyes, deterioration (including damage) of the structural materials, such as columns, beams, and foundations, caused by a leak in the roof or tremor of an earthquake can be easily and quickly discovered. Therefore, the structure in which the structural materials can be checked with eyes allows easily monitoring the health (soundness) of the entire structural materials and allows performing appropriate maintenance.

However, many parts of a structure, such as a wooden house, of recent years cannot be visually recognized due to a finishing material. Therefore, the finishing Material needs to be removed to visually recognize the state of the structural materials.

Conventionally, an example of a technique for monitoring the shake of the structural materials difficult to visually recognize includes a technique disclosed in Japanese Patent Laid-Open No. 2001-242112 (Patent Document 1). A maintenance and management apparatus of a foundation wood section disclosed in Patent Document 1 includes: electrodes driven into the foundation wood section; and lead wires connected to the electrodes and drawn outdoors. Therefore, moisture content can be measured from outside, and whether the foundation wood section is prone to decay can be monitored without going under the floor to work.

However, the conventional technique monitors only the deterioration of the foundation wood (wood still) section caused by moisture, and is difficult to monitor the health of the entire structural materials.

The section that deteriorates is not limited to the foundation wood (wood still) section among the structural materials. Furthermore, the cause of the deterioration is not limited to moisture. For example, joint portions of structural materials, such as columns and beams, may be displaced or detached due to an earthquake. The structural materials may also be cracked due to an earthquake or deterioration over time.

For a structure in which it is difficult to monitor the health of the entire structural materials, it is difficult to appropriately perform maintenance to counter the deterioration in order to keep the structure in a sound state for a long time. Meanwhile, it is too cumbersome and is difficult to execute a monitoring method of periodically performing work of removing the finishing material to surely monitor the health of the entire structural materials, inspecting the health of the structural materials, performing maintenance as necessary, and putting the finishing material back again.

SUMMARY OF THE INVENTION

The present invention has been made in light of the above situation, and accordingly it is an object of the present invention to provide a structural health monitoring apparatus and a structural health monitoring method that can non-destructively and easily monitor health of a structure.

To solve the above problem, the structural health monitoring apparatus according to an aspect of the present invention is a structural health monitoring apparatus for monitoring health of a structure includes a resistance measurement unit and an evaluation unit. The structure for monitoring includes an assembled body and a plurality of structural materials. The plurality of structural materials forms the assembled body, and each structural material has joint portions and a shaft portion. At least part of surfaces of the joint portions and at least part of surfaces of the shaft portion are conductive such that, by surfaces of the plurality of structural materials being electrically connected, electrical paths are formed in the assembled body that forms frames of a three-dimensional building assembled by joining the plurality of structural materials through the joint portions. The resistance measurement unit of the structural health monitoring apparatus measures a resistance value between one terminal and another terminal of a set of two terminals. The set of two terminals is selected from a plurality of terminals provided on the electrical paths. The resistance value being measured is a combined resistance value of all electrical paths from the one terminal to the other terminal of the set of two terminals. The evaluation unit evaluates the health of the structure by using a difference between the resistance value between terminals of the set of two terminals measured by the resistance measurement unit and a reference resistance value between terminals of the set of two terminals, and outputs evaluation result information.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of a structural health monitoring apparatus and a structural health monitoring method according to embodiments of the present invention with reference to the drawings. Note that the following description illustrates an example in which a structure to be monitored by the structural health monitoring apparatus according to the present invention is a wooden building.

First Embodiment

Figure 1:
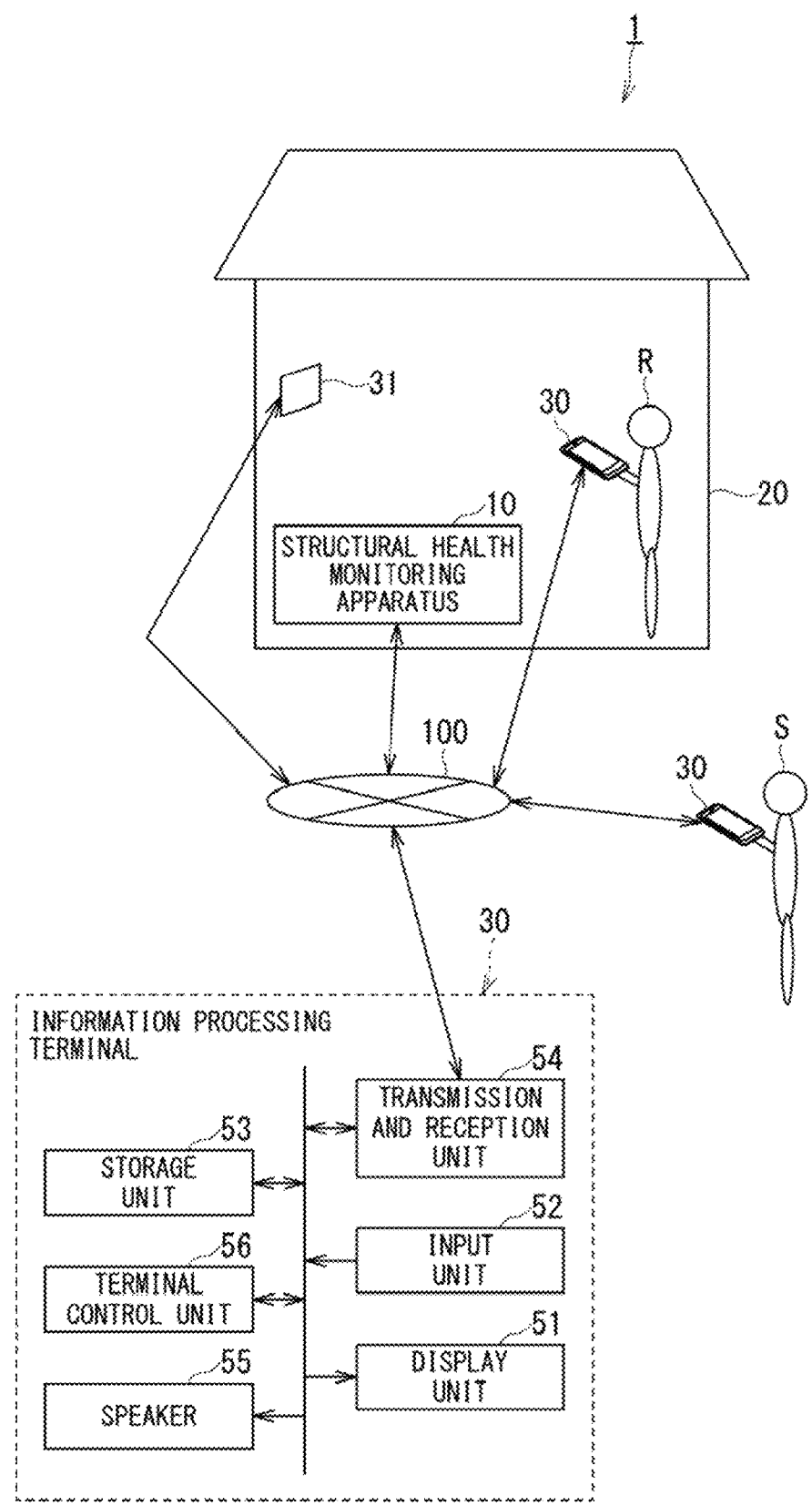
FIG. 1 is a block diagram showing an example of a structural health monitoring system including a structural health monitoring apparatus according to a first embodiment of the present invention.

FIG. 1 is a block diagram showing an example of a structural health monitoring system 1 including a structural health monitoring apparatus 10 according to a first embodiment of the present invention. Note that the following description illustrates an example in which the structure to be monitored by the structural health monitoring apparatus 10 according to the present invention is a wooden building.

The structural health monitoring system 1 includes the structural health monitoring apparatus 10, a structure 20, and a display terminal. The display terminal is a terminal device having at least a display function and is used by an observer (resident R or service man S). The display terminal as the terminal device may be an information processing terminal 30 connected to the structural health monitoring apparatus 10 through a network 100 in a manner that data can be transmitted and received or may be a monitor 31 provided on a wall or the like in the structure 20. In the present embodiment, the structural health monitoring apparatus 10 is installed inside of the structure 20 and is connected to the information processing terminal 30 or the monitor 31 through the network 100 in a manner that data can foe transmitted and received.

Figure 2A:
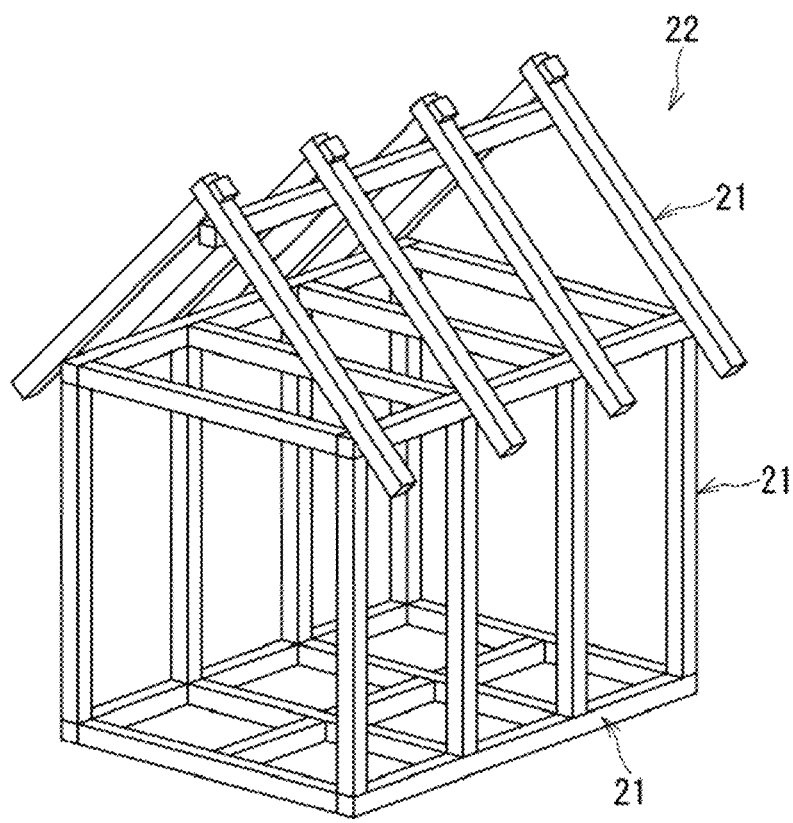
FIG. 2A is an explanatory diagram showing an example of an assembled body including a plurality of structural materials.
Figure 2B:
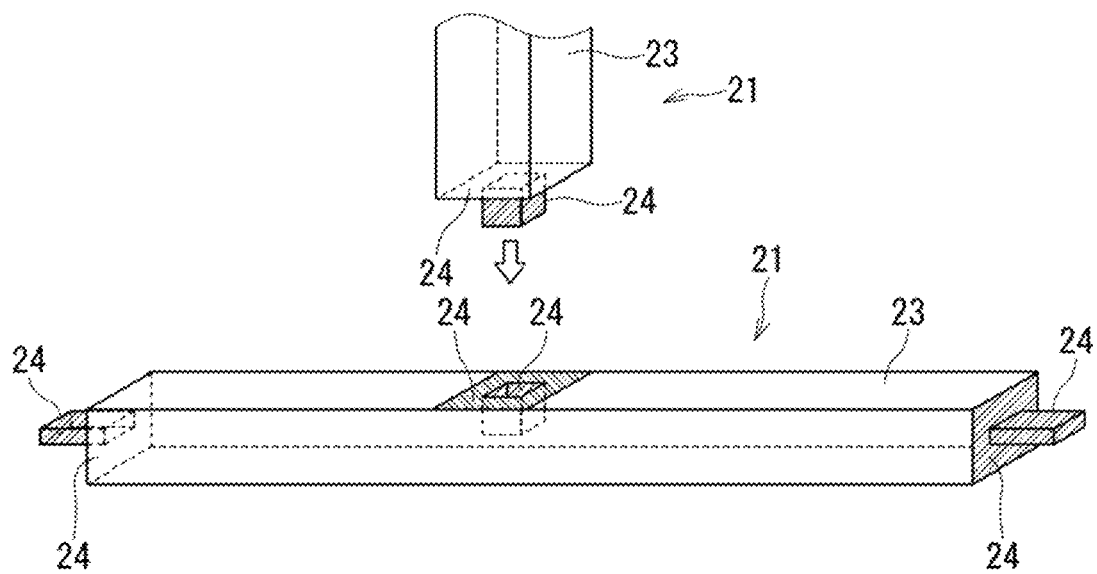
FIG. 2B is an explanatory diagram showing an example of a configuration of the structural materials.

FIG. 2A is an explanatory diagram showing an example of an assembled body 22 including a plurality of structural materials 21, and FIG. 2B is an explanatory diagram showing an example of a configuration of the structural materials 21.

As shown in FIG. 2B, each of the structural materials 21 includes a shaft portion 23 and joint portions 24. The plurality of structural materials 21 are joined and assembled through the joint portions 24 (see hatching in FIG. 2B), such as so-called couplers and connections, to form the assembled body 22 (see FIG. 2A). A finishing material is used over the assembled body 22 to complete the structure 20. In the assembled body 22, the structural, materials 21 function as columns, horizontal members, foundations, diagonal braces, and the like.

A conductive paint is applied to at least part of surfaces of the shaft portions 23 and at least part of surfaces of the joint portions 24 to form conductive films on the structural materials 21 so that surfaces of the plurality of structural materials 21 are electrically connected to form electrical paths when the assembled body 22 is constructed. In other words, the conductive films on the surfaces of the structural materials 21 form electrical circuits (resistance dividers) in the assembled body 22.

When conductive sections are part of the surfaces of the joint portion 24, corresponding positions facing each other in the structural materials 21 to be joined are the part. When conductive sections are part of the surfaces of the shaft portions 23, positions of the electrical paths connecting the conductive sections of the joint portions 24 are the part.

The conductive paint may be applied to the entire surfaces of the structural materials 21 (entire surfaces of the joint portions 24 and the shaft portions 23) to form the conductive films to completely cover the structural materials 21 with the conductive films. In this case, a material that is effective in increasing the life of the wood forming the structural materials 21 is preferable to be used as a conductive paint. For example, some conductive paints containing bamboo charcoal powder have a bactericidal effect, a deodorizing effect, and a moisture intrusion prevention effect because of hydrophilic surface, when the conductive paint is applied to a wood surface. The bactericidal effect can reduce cellulose decomposition caused by decay fungi, and this type of paint containing bamboo charcoal has a preservative effect of wood and an effect of reducing attraction of termites that may be caused by the cellulose decomposition. The hardness of this type of paint containing bamboo charcoal makes it difficult for the termites to bite. Therefore, an anti-termite effect can also be expected by applying this type of paint containing bamboo charcoal on the entire surface of the wood.

Note that the surfaces of the shaft portion 23 may not be exposed surfaces (outermost surfaces) as long as the electrical paths are formed by the surfaces of the shaft portion 23 and the surfaces of the joint portions 24 when the assembled body 22 is constructed. For example, after the assembled body 22 is constructed, non-conductive films may be further formed over the conductive films provided on the surfaces of the shaft portions 23. Furthermore, the conductive films may not be formed on the entire surfaces of the structural materials 21 before the assembled body 22 is assembled as long as the assembled body 22 includes the electrical paths formed by the surfaces of the shaft portions 23 and the surfaces of the joint portions 24. For example, the conductive films may be formed in advance only on the surfaces of the joint, portions 24 of the structural materials 21 and the surfaces of the shaft portions 23 near the joint portions 24, and the conductive films may be formed on the remaining part of the shaft portions 23 necessary to form the electrical paths after the assembled body 22 is constructed by assembling the structural materials 21.

Figure 3A:
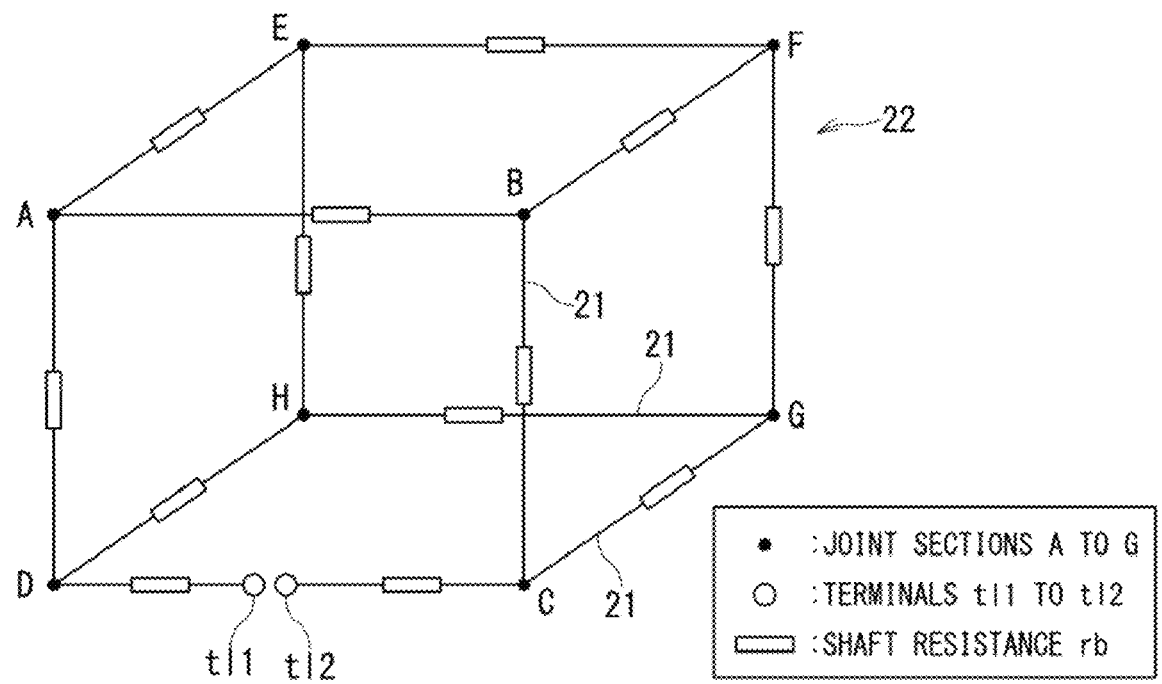
FIG. 3A is an explanatory diagram schematically showing an example of an electrical circuit formed by the assembled body and a terminal group tl including two terminals tl1 and tl2.
Figure 3B:
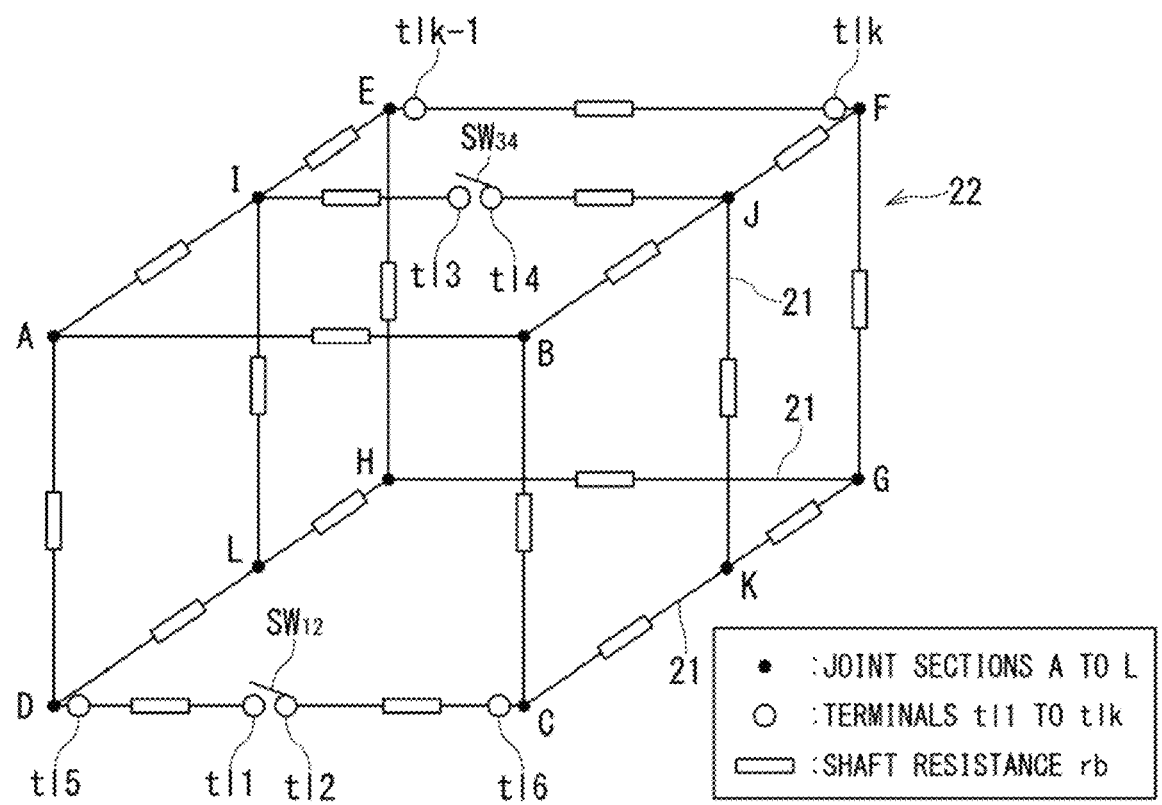
FIG. 3B is an explanatory diagram schematically showing another example of the electrical circuit formed by the assembled body and the terminal group tl including k pieces of terminals tl1 to tlk.

FIG. 3A is an explanatory diagram schematically showing an example of an electrical circuit formed by the assembled body 22 and a terminal group tl including two terminals tl1 and tl2. FIG. 3B is an explanatory diagram schematically showing another example of the electrical circuit formed by the assembled body 22 and the terminal group tl including k pieces of terminals tl1 to tlk. In FIGS. 3A and 3B, the joint sections are indicated by alphabets A to L. FIG. 3A illustrates an example in which the assembled body 22 includes the terminal group tl including two terminals tl1 and tl2, and FIG. 3B illustrates an example in which the assembled body 22 includes the terminal group tl including k pieces of (wherein, k is an integer equal to or greater than 2) terminals tl1 to tlk.

As shown in FIG. 3A, the assembled body 22 is provided with at least two terminals tl1 and tl2. The assembled body 22 may be provided with three or more terminals as shown in FIG. 3B. The terminals tl1 to tlk are provided on the electrical paths of the surfaces of the structural materials 21.

A resistance between two terminals is a combined resistance of a shaft resistance rb and a joint resistance rj on the electrical path between two terminals. A resistance value between terminals of a predetermined set of two terminals (for example, tl1 and tl2) is a same value regardless of measurement time as long as there is no change in the shaft resistance rb and the joint resistance rj. On the other hand, for example, the resistance value between terminals changes when an earthquake or the like changes a joint state of the joint sections due to so-called detachment or displacement or when a state of the shaft portions 23 changes due to a so-called crack.

For example, when the structural material 21 connecting the joint sections A and B is separated from the joint section A, the electrical path connecting the joint sections A and B opens. Therefore, the combined resistance value of the electrical path between terminals of the terminal tl1 and the terminal tl2 increases when, for example, the electrical path connecting the joint sections A and B opens. Thus, it can be understood that the resistance value between two terminals is a value reflecting the joint state of the joint sections or the state of the shaft portions 23.

Therefore, the structural health monitoring apparatus 10 according to the present embodiment monitors the resistance value between two terminals provided on the electrical path to monitor the change in the joint state of the joint sections and the change in the state of the shaft portions 23 in the structure 20 in which the surfaces of the plurality of structural materials 21 are electrically connected to form electrical paths.

Figure 4:
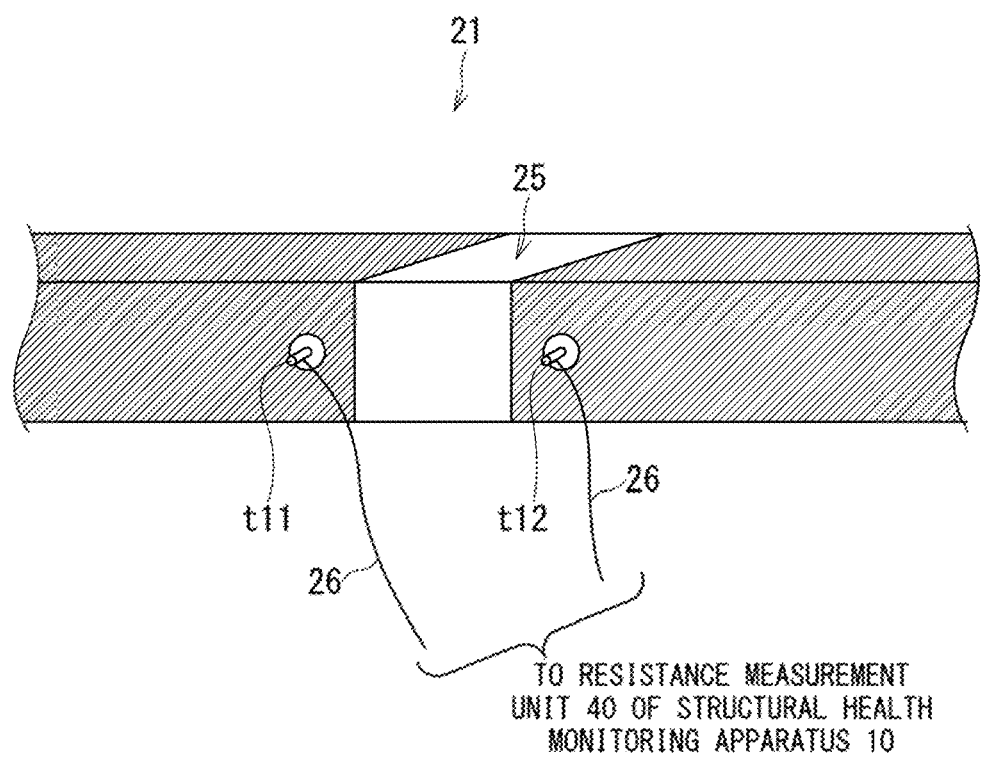
FIG. 4 is an explanatory diagram showing an example in which an insulating portion is provided between terminals.

FIG. 4 is an explanatory diagram showing an example in which an insulating portion 25 is provided between terminals. In FIG. 4, a hatched section indicates the conductive film.

The insulating portion 25 can be provided between two terminals provided on the same structural material 21, in which the distance between two terminals is shorter than a predetermined distance, among the sets of two terminals (see FIG. 4). Note that FIG. 4 illustrates an example in which the terminals tl1 and tl2 are posts, and lead wires 26 connected to the posts are connected to a resistance measurement unit 40. However, the terminals tl1 to tlk are not limited to the posts, and for example, recessed shapes, such as banana sockets, may be formed on the structural materials 21.

Furthermore, drawer members, such as posts, and the lead wires 26 may not be necessary, and the observer may directly bring tester terminals or the like into contact with two sections on the electrical path upon the measurement of the resistance. For example, in the example illustrated in FIG. 3, the terminals tl1 and tl2 may be provided in an underfloor storage hole that can be accessed by the observer (resident R or service man S), and the terminals tl3 and tl4 may be provided in a ceiling inspection hole that can be accessed by the observer (resident R or service man S).

In addition, when the insulating portion 25 is provided, a switch SW for short-circuiting the two terminals across the insulating portion 25 may be provided. FIG. 3B illustrates an example in which a switch $SW_{12}$ is provided between the terminals tl1 and tl2, and a switch $SW_{34}$ is provided between the terminals tl3 and tl4.

Furthermore, when the switches SW are provided, the switch corresponding to the set of two terminals to be measured can be opened, and the switch corresponding to the set of two terminals not to be measured can be short-circuited in order to secure the electrical path except the terminals to be measured. For example, when the resistance value between the terminals tl1 and tl2 is to be measured in the example illustrated in FIG. 3B, the switch $SW_{12}$ between the terminals tl1 and tl2 can be opened, and the switch $SW_{34}$ between the terminals tl3 and tl4 can be short-circuited.

Figure 5:
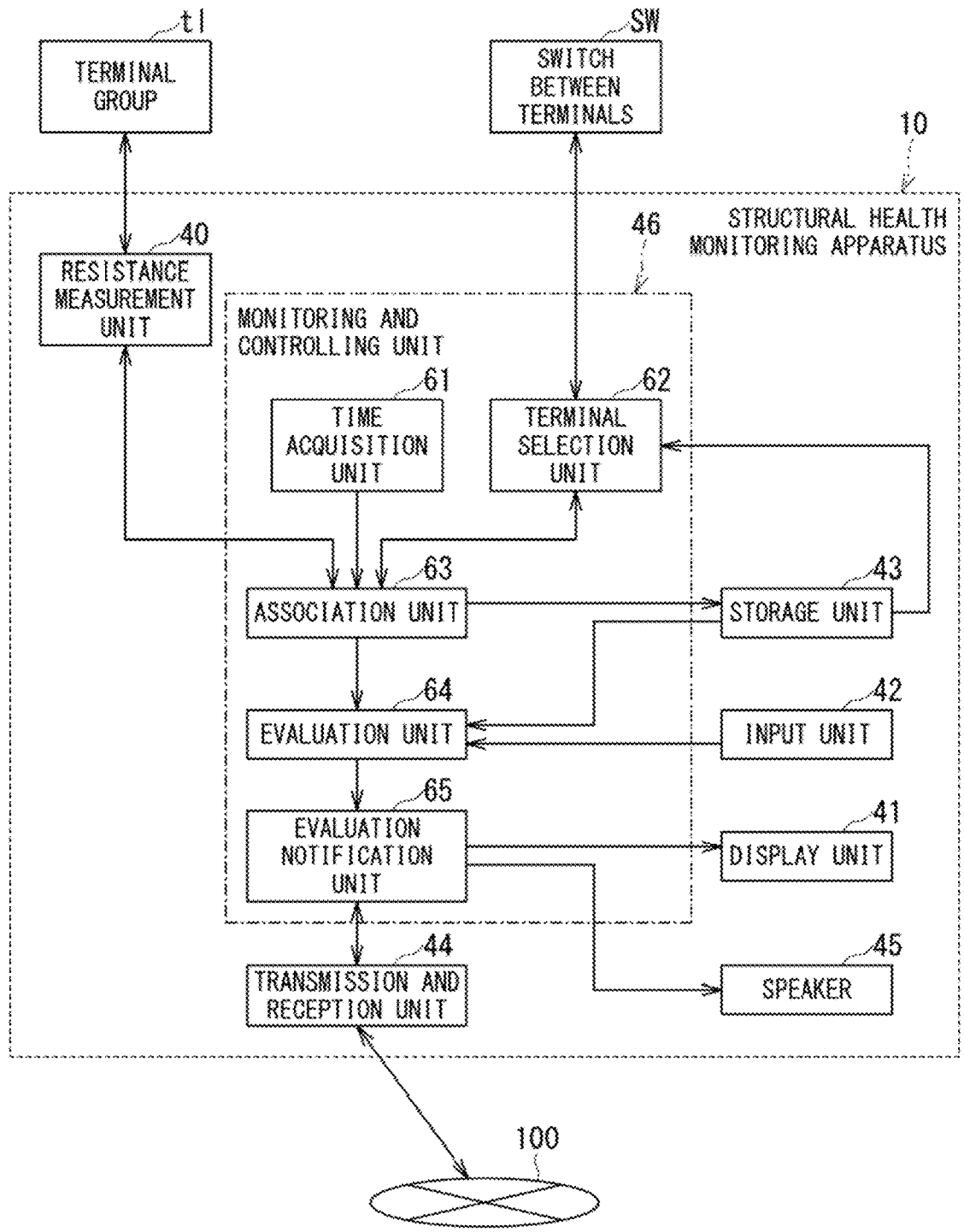
FIG. 5 is a block diagram schematically showing an example of internal configuration of the structural health monitoring apparatus according to the first embodiment.

FIG. 5 is a block diagram schematically showing an example of internal configuration of the structural health monitoring apparatus 10 according to the first embodiment.

The structural health monitoring apparatus 10 includes a display unit 41, an input unit 42, a storage unit 43, a transmission and reception unit 44, a speaker 45, and a monitoring and controlling unit 46, in addition to the resistance measurement unit 40. The units 41 to 46 excluding the resistance measurement unit 40 can be, for example, a general personal computer, a work station, or a portable information processing terminal such as a tablet terminal.

The display unit 41 is, for example, a general display output apparatus, such as a liquid crystal display and an OLED (Organic Light Emitting Diode) display, and is configured to display various images, such as images indicating health (soundness) of the structure 20, according to control by the monitoring and controlling unit 46.

The input unit 42 is, for example, a general input apparatus, such as a mouse, a trackball, a keyboard, a touch panel, and a numeric keypad. The input unit 32 outputs an operation input signal corresponding to an operation by the observer to the monitoring and controlling unit 46. A microphone for inputting a speech may also be used as the input unit 42. In this case, the microphone converts the speech input by the observer to a digital speech signal, and the monitoring and controlling unit 46 applies a speech recognition process to the digital speech signal to perform an operation according to the speech input by the observer.

The storage unit 43 includes recording media readable and writable toy a CPU of the monitoring and controlling unit 46, such as a magnetic or optical recording medium and a semiconductor memory, and part or all of programs and data in the storage may be downloaded through the network 100. The storage unit 43 stores reference resistance values and association information.

The transmission and reception unit 44 is provided with various information communication protocols according to a mode of the network 100. The transmission and reception unit 44 connects the structural health monitoring apparatus 10 to the information processing terminal 30 and the monitor 31 according to the various protocols in a manner that data can be transmitted and received. Here, the network 100 denotes an information communication network in general using a telecommunication technique and includes a wireless/wired LAN (Local Area Network) and the Internet, as well as a telephone communication network, an optical fiber communication network, a cable communication network, a satellite communication network, and the like.

The speaker 45 outputs a speech, a beep, and the like corresponding to various pieces of information, such as warning information for alerting the observer, when evaluation result information output by the monitoring and controlling unit 46 includes information indicating that there is an abnormality in the structure 20.

Note that the "speech" here is a sound that reads out text data by using a sound that a listener recognizes as a voice of a person. The "sound" includes "speech" und also includes "music", "sound effect (such as a beep)", and the like.

The monitoring and controlling unit 46 includes a CPU, a storage medium, such as a RAM and a ROM, and the like, and for example, a one-chip microcomputer can be used for the monitoring and controlling unit 46. The monitoring and controlling unit 46 controls the operation of the structural health monitoring apparatus 10 according to a program stored in the storage medium. The CPU of the monitoring and controlling unit 45 loads, on the RAM, a monitoring program stored in the storage medium, such as a ROM, and data necessary for executing the program. The CPU follows the pro-gram to execute a process of measuring the resistance values of the electrical paths formed on the assembled body 22 to non-destructively and easily monitor the health of the structure 20.

Note that the display unit 41, the input unit 42, and the speaker 45 may not be provided on the structural health monitoring apparatus 10.

Meanwhile, the information processing terminal 30 can be a general personal computer, a work station, a portable information processing terminal, such as a tablet terminal, or the like. As shown in FIG. 1, the information processing terminal 30 includes a display unit 51, an input unit 52, a storage unit 53, a transmission and reception unit 54, a speaker 55, and a terminal control unit 56. Note that the input unit 52 and the speaker 55 may not be provided on the information processing terminal 30.

The display unit 51, the input unit 52, and the speaker 55 have configurations equivalent to the display unit 41, the input unit 42, and the speaker 45 of the structural health monitoring apparatus 10.

The display unit 51 displays various images, such as an image indicating the health of the structure 20, received from the monitoring and controlling unit 46 through the network 100.

The display unit 51 and the input unit 52 may foe integrated to form an operation panel. In this case, the operation panel includes: hard keys as part of the input unit 52, such as buttons for providing specific instruction signals to the CPU when pressed by the observer; and a display and input apparatus. In this case, the display and input apparatus includes the display unit 51 and a touch panel as part of the input unit 52 provided near the display unit 51. The display unit 51 is controlled by the terminal control unit 56 to display the image indicating the health of the structure 20, as well as information for operating the information processing terminal 30 and a plurality of soft keys for operating the information processing terminal 30. The touch panel provides information of a position on the touch panel instructed by the observer to the terminal control unit 56.

The storage unit 53 has a configuration equivalent to the storage unit 43 of the structural health monitoring apparatus 10, and part or aid of the programs and the data in the storage media may be downloaded through the network 100. The storage unit 53 may be controlled by the terminal control unit 56 to store the association information received from the monitoring and controlling unit 46 through the network 100.

The terminal control unit 56 includes a CPU, a storage medium, such as a RAM and a ROM, and the like. The terminal control unit 56 controls the operation of the information processing terminal 30 according to a program stored in the storage medium.

The monitor 31 has a configuration equivalent to at least the display unit 51 and the transmission and reception unit 54 of the information processing terminal 30 and displays various images, such as an image indicating the health of the structure 20, received from the monitoring and controlling unit 46 through the network 100.

Next, a configuration of the monitoring and controlling unit 46 of the structural health monitoring apparatus 10 will be described.

As shown in FIG. 5, the CPU of the monitoring and controlling unit 46 functions as at least a time acquisition unit 61, a terminal selection unit 62, an association unit 63, an evaluation unit 64, and an evaluation notification unit 65 through a monitoring program. The units 61 to 65 use a predetermined work area of the RAM as a temporary storage area of data. Note that these function realization units may fee realized by cooperation of a plurality of processors or may be realized by hardware logic, such as a circuit, without using the CPU.

The time acquisition unit 61 acquires information of current time based on output of an RTC (Real Time Clock) or an HPET (High Precision Event Timer) not shown.

The terminal selection unit 62 selects one or a plurality of sets of two terminals set in advance, from the terminal group tl (terminals tl1 to tlk). The terminal selection unit 62 controls the switches SW to open the switch SW corresponding to the set to be measured end short-circuit the switch SW corresponding to the set not to be measured. The resistance measurement unit 40 measures a current resistance value between terminals of the set or two terminals, for each of one or a plurality of sets of two terminals selected by the terminal selection unit 62.

For example, when the resistance measurement unit 40 includes a set of positive and negative measurement terminals, and the terminal selection unit 62 selects a plurality of sets of two terminals, the selected sets of two terminals are sequentially connected to the measurement terminals of the resistance measurement unit 40. In this case, the resistance measurement unit 40 sequentially measures the resistance values between terminals of the sets of two terminals connected to the measurement terminals. The resistance measurement unit 40 charges a capacitor with, for example, a high-voltage DC and applies the high voltage to between the measurement terminals to thereby detect a current flowing between the measurement terminals to measure the resistance values between terminals of the sets of two terminals.

Note that the terminal selection unit 62 and the switches SW may not be provided when only one set of two terminals is selected instead of a plurality of sets of two terminals, such as when the number of terminals is two.

The terminal selection unit 62 may also select one or a plurality of sets of two terminals based on an instruction by the observer through the input unit 42, the input unit 52 of the information processing terminal 30, or an input unit not shown of the monitor 31. In this case, an image for receiving a selection of terminals by the observer may be displayed on the display unit 41, the display unit 51 of the information processing terminal 30, or the monitor 31.

Figures 6, 7:
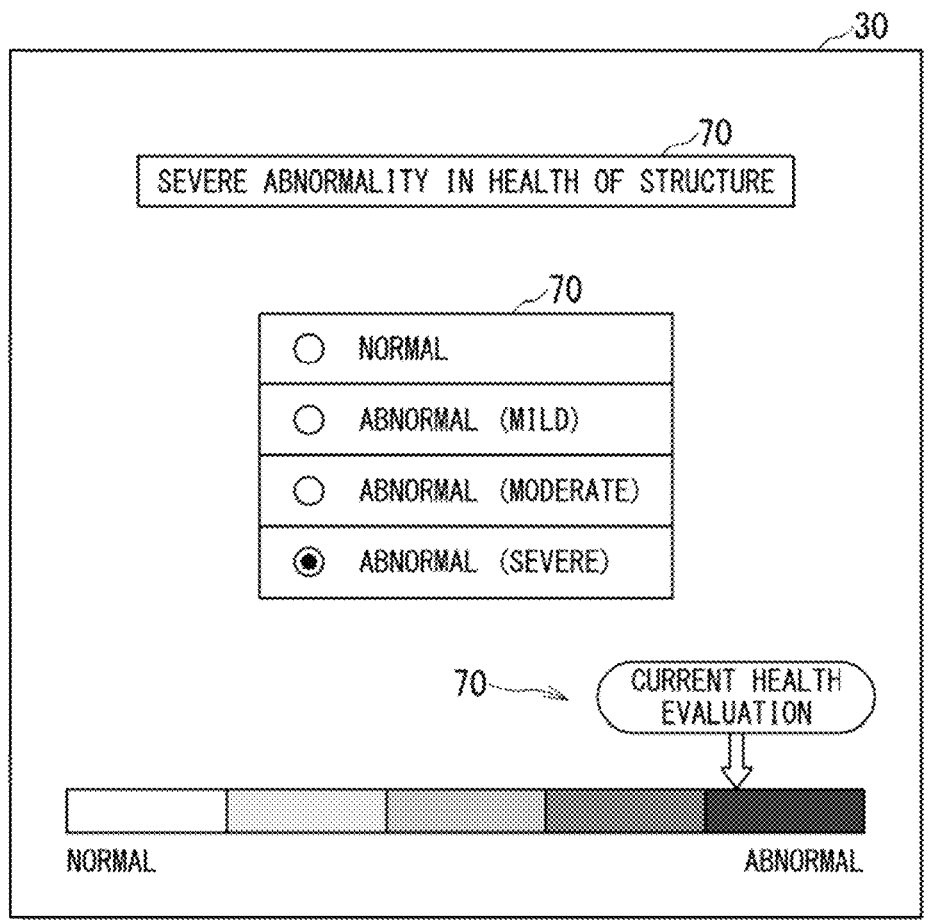
FIG. 6 is an explanatory diagram showing an example of the association information.
FIG. 7 is an explanatory diagram showing an example in which an image according to the evaluation result information of the current health of the structure is displayed on the display unit of the information processing terminal.

FIG. 6 is an explanatory diagram showing an example of the association information. The evaluation unit 64 uses the association information as data for evaluating the current health of the structure 20.

The association unit 63 generates association information associating information of i sets of two terminals (wherein, i=1, 2, ..., m, and m is a positive integer) selected from the terminal group tl, resistance measurement values Ri(t) between terminals of the i sets of two terminals measured by the resistance measurement unit 40, end time t of the resistance measurement and stores the association information in the storage unit 43 (see FIG. 6).

The evaluation unit 64 uses a difference between the current resistance value between terminals of the set of two terminals and the reference resistance value between terminals of the set of two terminals to evaluate the health of the structure 20 and outputs and provides evaluation result information to the evaluation notification unit 65. In this case, the evaluation unit 64 can evaluate the health of the structure 20 in a plurality of levels including at least a normal state and a severely abnormal state to generate the evaluation result information.

Here, the health evaluation method of the structure 20 by the evaluation unit 64 will be more specifically described.

The evaluation unit 64 may use, as the reference resistance value, an initial resistance value between terminals of the set of two terminals. The initial resistance value denotes, for example, a resistance value (see t=tl in FIG. 6) measured in advance at a predetermined measurement timing in a predetermined period (in an initial period) after the assembled body 22 is constructed by joining and assembling the plurality of structural materials 21 through the joint portions 24. Here, examples of the measurement timing m the initial period include just after the construction of the assembled body 22 and just after the completion of the structure 20. In this case, the evaluation unit 64 evaluates the health of the structure 20 according to a difference between the current resistance value between terminals of the set of two terminals and the initial resistance value between terminals of the set of two terminals.

The evaluation unit 64 may also use, as the reference resistance value, a current predicted resistance value between terminals of the set of two terminals that is a resistance value obtained by predicting a change over time of the resistance value from the initial period to the current time and correcting the initial resistance value between terminals of the set of two terminals. In this, case, a correction formula, a correction lookup table, and the like for predicting the change over time can foe stored in advance in the storage unit 43, and the formula and the table can be used to obtain the current predicted resistance value.

Note that it can tee evaluated that the structure 20 is sound when the difference between the current resistance value between terminals of the set of two terminals and the reference resistance value between terminals of the set of two terminals is within a predetermined threshold. For example, the structure 20 is exposed to mild vibration on a daily basis when the structure 20 is a building and is exposed to strong winds, when the structure 20 is close to a road with heavy traffic or close to a construction site, and so forth. In this case, fluctuations in the resistance value is observed on a daily basis. Therefore, it can be evaluated that the structure 20 is sound when the difference between the current resistance value between terminals of the set of two terminals and the reference resistance value between terminals of the set of two terminals is within the predetermined threshold.

The evaluation unit 64 may also extract a history of the resistance measurement value from a history of the association information and evaluate the health of the structure 20 based on the history of the resistance measurement value. For example, the evaluation unit 64 may evaluate that there is an abnormality in the structure 20 when the difference between the current resistance value between terminals of the set of two terminals and the reference resistance value between terminals of the set of two terminals exceeds a first threshold for a predetermined number of times or more or for a predetermined period or more. In this case, the evaluation unit 64 may evaluate that there is a severe abnormality in the structure 20 when the difference between the current resistance value between terminals of the set of two terminals and the reference resistance value between terminals of the set of two terminals is equal to or greater than a second threshold larger than the first threshold.

Note that the measurement of the resistance value by the resistance measurement unit 40 and the generation of the association information by the association unit 63 can be periodically performed, such as every hour, every day, and every week. In addition to the periodic measurement of the resistance value and the generation of the association information, the measurement of the resistance value and the generation of the association information may be performed at a necessary timing based on an instruction by the observer through the input unit 42, the input unit 52 of the information processing terminal 30, or the input unit not shown of the monitor 31.

Furthermore, the timing of the evaluation of the health by the evaluation unit 64 may be in accordance with the timing of the generation of the association information or may be a periodic timing (for example, every day) different from the timing of the generation of the association information (for example, every hour). The health (soundness) can be periodically evaluated to monitor the health of the structure 20 all the time. Obviously, in addition to the periodic evaluation of the health, the health may be evaluated at a necessary timing based on an instruction by the observer through the input unit 42, the input unit 52 of the information processing terminal 30, or the input unit not shown of the monitor 31.

When there are i sets of two terminals, evaluation result information indicating that there is an abnormality in the structure 20 may be generated if there is an abnormality in one set, or the evaluation result information indicating that there is an abnormality in the structure 20 may be generated only if there are abnormalities in a predetermined number of sets.

FIG. 7 is an explanatory diagram showing an example in which an image 70 according to the evaluation result information of the currant health of the structure 20 is displayed on the display unit 51 of the information processing terminal 30.

The evaluation notification unit 65 generates information according to the evaluation result information of the current health of the structure 20 output by the evaluation unit 64 and presents the information to the observer.

For example, the evaluation notification unit 65 generates the image 70 according to the evaluation result information of the current health of the structure 20 output by the evaluation unit 64 and causes the display unit 41, the monitor 31, and the display unit 51 of the information processing terminal 30 to display the image 70. The evaluation notification unit 65 also causes the speakers 45 and 55 to output a speech or a beep containing warning information for alerting the observer when the evaluation result information output by the monitoring and controlling unit 46 includes information indicating that there is an abnormality in the structure 20. The evaluation notification unit 65 may also generate an email containing the evaluation result information of the current health and transmit the email to the information processing terminal 30.

The image 70 may foe a character string indicating the current health evaluation (see upper part or FIG. 7), may be an image indicating any level of the current health among a plurality of levels including the normal state and the severely abnormal state (see middle part of FIG. 7), or may be an image using a color bar or the like that allows intuitively and easily understand the current health evaluation (see lower part of FIG. 7).

The evaluation notification unit 65 may transmit the image 70 to the display unit 51 of the information processing terminal 30 only when the evaluation result information output by the monitoring and controlling unit 46 includes information indicating that there is an abnormality in the structure 20. The evaluation notification unit 65 may generate the email containing the evaluation result information of the current health and transmit the email to the information processing terminal 30 only when the evaluation result information includes information indicating that there is an abnormality in the structure 20. The evaluation notification unit 65 may transmit the email just to the information processing terminal 30 possessed by the service man S when the health evaluation of the evaluation result information is normal or mildly abnormal. When there is a severe abnormality, the evaluation notification unit 65 may transmit the warning email not only to the information processing terminal 30 possessed by the service man S, but also to the information processing terminal 30 possessed by the resident R, may cause the display unit 41, the display unit 51 of the information processing terminal 30, and the monitor 31 to display the image 70, and may cause the speaker 45, the speaker 55 of the information processing terminal 30, and the speaker not shown of the monitor 31 to output the speech or the beep containing the warning information.

Next, an example of operation of the structural health monitoring apparatus and the structural health monitoring method according to the present embodiment will be described.

Figure 8:
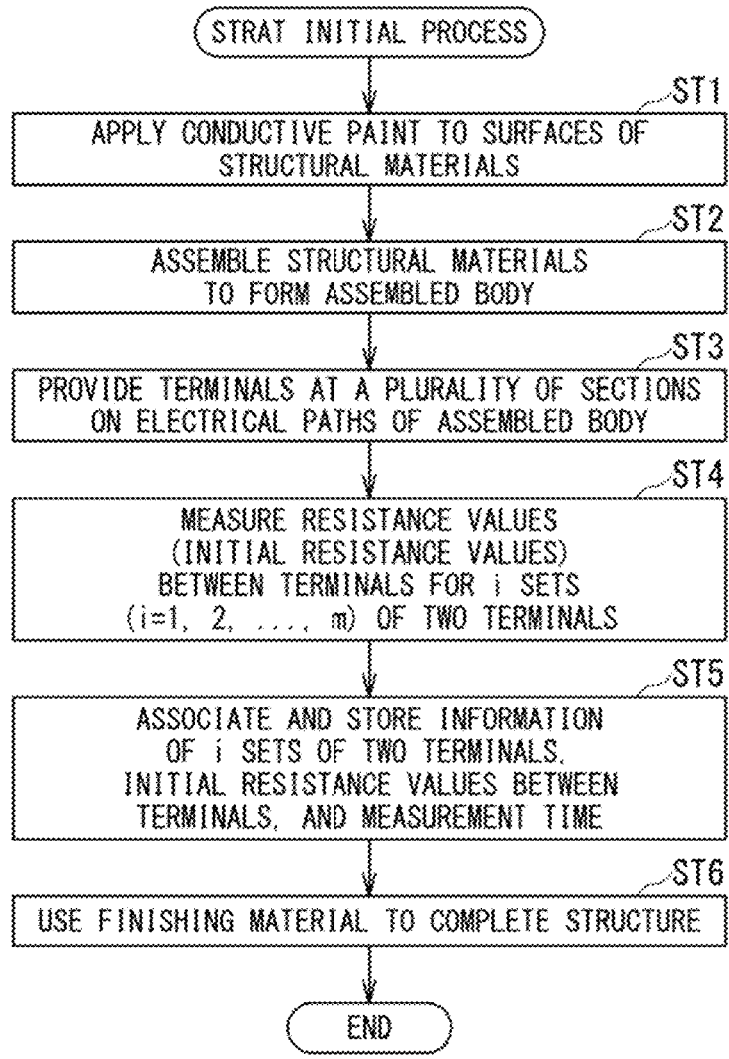
FIG. 8 is a flow chart showing an example of a procedure in which the CPU of the structural health monitoring apparatus shown in FIG. 1 executes a process of measuring initial resistance values when electrical paths on the assembled body is initially formed.

FIG. 8 is a flow chart showing an example of a procedure in which the CPU of the structural health monitoring apparatus 10 shown in FIG. 1 executes a process of measuring initial resistance values when electrical paths on the assembled body is initially formed. In FIG. 8, reference signs with numbers added to S indicate steps of the flow chart.

First, in step ST1, the conductive paint containing bamboo charcoal powder is applied to the entire surfaces including the joint portions 24 of the structural materials 21 made of wood. Next, in step ST2, the structural materials 21 are assembled to form the assembled body 22.

Next, in step ST3, the terminal group tl is provided at a plurality of sections on the electrical paths of the assembled body 22.

Next, in step ST4, the initial resistance values between terminals of the i sets of two terminals are measured within a predetermined period from the assembly of the assembled body 22.

Next, in step ST5, the information of the i sets of two terminals, the initial resistance values between terminals, and the measurement time are associated and stored in the storage unit 43.

Next, in step ST6, a finishing material is used to complete the structure 20.

The procedure allows forming the electrical paths on the assembled body 22 to measure the initial resistance values. Note that steps ST2 and 3 may be switched in the procedure. Furthermore, step ST6 may be performed after step ST3 and before ST4. Furthermore, step ST1 may be performed again after step ST2 and before ST3 to apply two coats of the conductive paint.

Figure 9:
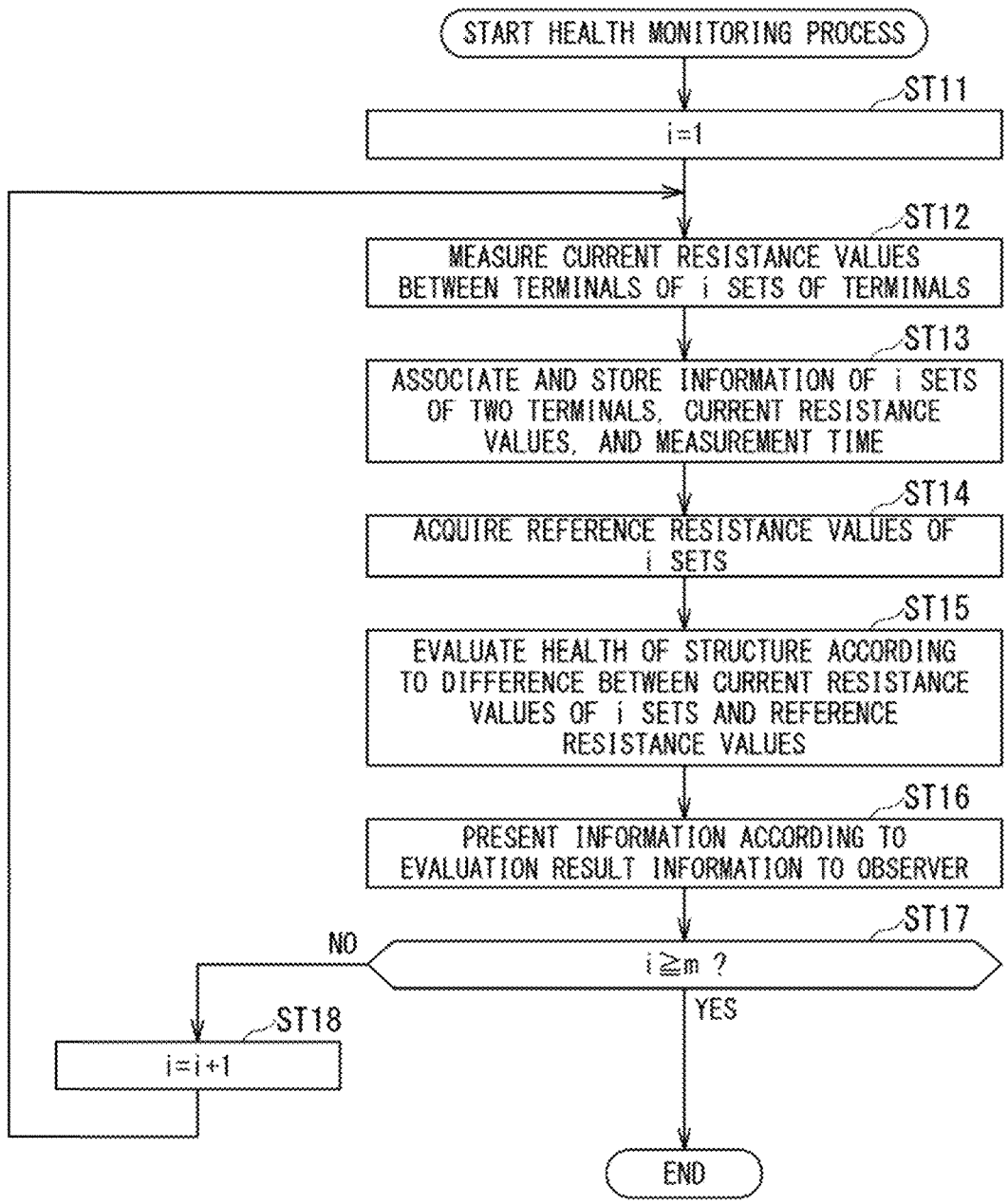
FIG. 9 is a flow chart showing an example of a procedure in which the CPU of the structural health monitoring apparatus of FIG. 1 measures the resistance values of the electrical paths formed on the assembled body to non-destructively and easily monitor the health of the structure.

FIG. 9 is a flow chart showing an example of a procedure in which the CPU of the structural health monitoring apparatus 10 of FIG. 1 measures the resistance values of the electrical paths formed on the assembled body 22 to non-destructively and easily monitor the health of the structure 20. In FIG. 9, reference signs with numbers added to S indicate steps of the flow chart. The procedure starts after the end of the procedure illustrated in FIG. 8.

In step ST11, the association unit 63 stores i=1 in a predetermined work area of the RAM. Next, in step ST12, the terminal selection unit 62 selects one or i sets of two terminals from the terminal group tl (terminals tl1 to tlk). The resistance measurement unit 40 then measures the current resistance values between terminals of the i sets of two terminals for each of one or i sets of two terminals selected by the terminal selection unit 62.

Next, in step ST13, the association unit 63 generates association information associating the information of the i sets of two terminals selected from the terminal group tl, the resistance measurement values Ri(t) between terminals of the i sets of two terminals measured by the resistance measurement unit 40, and the time t of the resistance measurement and stores the association information in the storage unit 43 (see FIG. 6).

Next, in step ST14, the evaluation unit 64 acquires the reference, resistance values of the i sets. For example, when the initial resistance values are the reference resistance values, the evaluation unit 64 acquires the initial resistance values of the i sets from the association information.

Next, in step ST15, the evaluation unit 64 uses the difference between the current resistance values between terminals of the i sets of two terminals and the reference resistance values between terminals of the i sets of two terminals to evaluate the health of the structure 20 and outputs and provides the evaluation result information to the evaluation notification unit 65.

Next, in step ST16, the evaluation notification unit 65 generates information (for example, the image 70) according to the evaluation result information of the current health of the structure 20 output by the evaluation unit 64 and presents the information to the observer.

Next, in step ST17, the association unit 63 determines whether the value of i stored in the predetermined work area of the RAM is equal to or greater than m that is a maximum value of i. If the value of i is equal to or greater than m, the series of procedure ends. On the other hand, if the value of i is smaller than m, 1 as added to the value of i stored in the predetermined work area of the RAM in step S18, and the procedure returns to step ST12.

The procedure allows measuring the resistance values of the electrical paths formed on the assembled body 22 to non-destructively and easily monitor the health of the structure 20.

The structural health monitoring apparatus 10 according to the present embodiment can measure the resistance values of the electrical paths formed on the assembled body 22. The resistance values of the electrical paths formed on the assembled body 22 are values reflecting the joint state of the joint sections and the state of the shaft portions 23. Therefore, according to the structural health monitoring apparatus 10 of the present embodiment, the current health of the structure 20 can be non-destructively and easily monitored. Furthermore, according to the structural health monitoring apparatus 10 of the present embodiment, the monitoring can fee performed all the time, and the observer can be surely notified of the abnormality when there is an abnormality.

For example, when there is a big earthquake, the joint sections of the assembled body 22 may be detached or displaced, or the structural materials 21 may be cracked, even, though there is no abnormality in the structure 20 in appearance. In this case, the structure 20 may suddenly collapse when there is an aftershock. Even in such a case, the structural health monitoring apparatus 10 according to the present embodiment can surely detect the change in the resistance value caused by the detachment or the displacement of the joint sections of the assembled body 22 or the crack of the structural materials 21 due to the first earthquake and can notify the observer of the abnormality.

Furthermore, the current health of the structure 20 can be non-destructively and appropriately evaluated, and the value of the structure 20 can be appropriately evaluated when the structure 20 is to be sold.

Second Embodiment

Next, a second embodiment of the structural health monitoring apparatus and the structural health monitoring method according to the present invention will be described.

Figure 10:
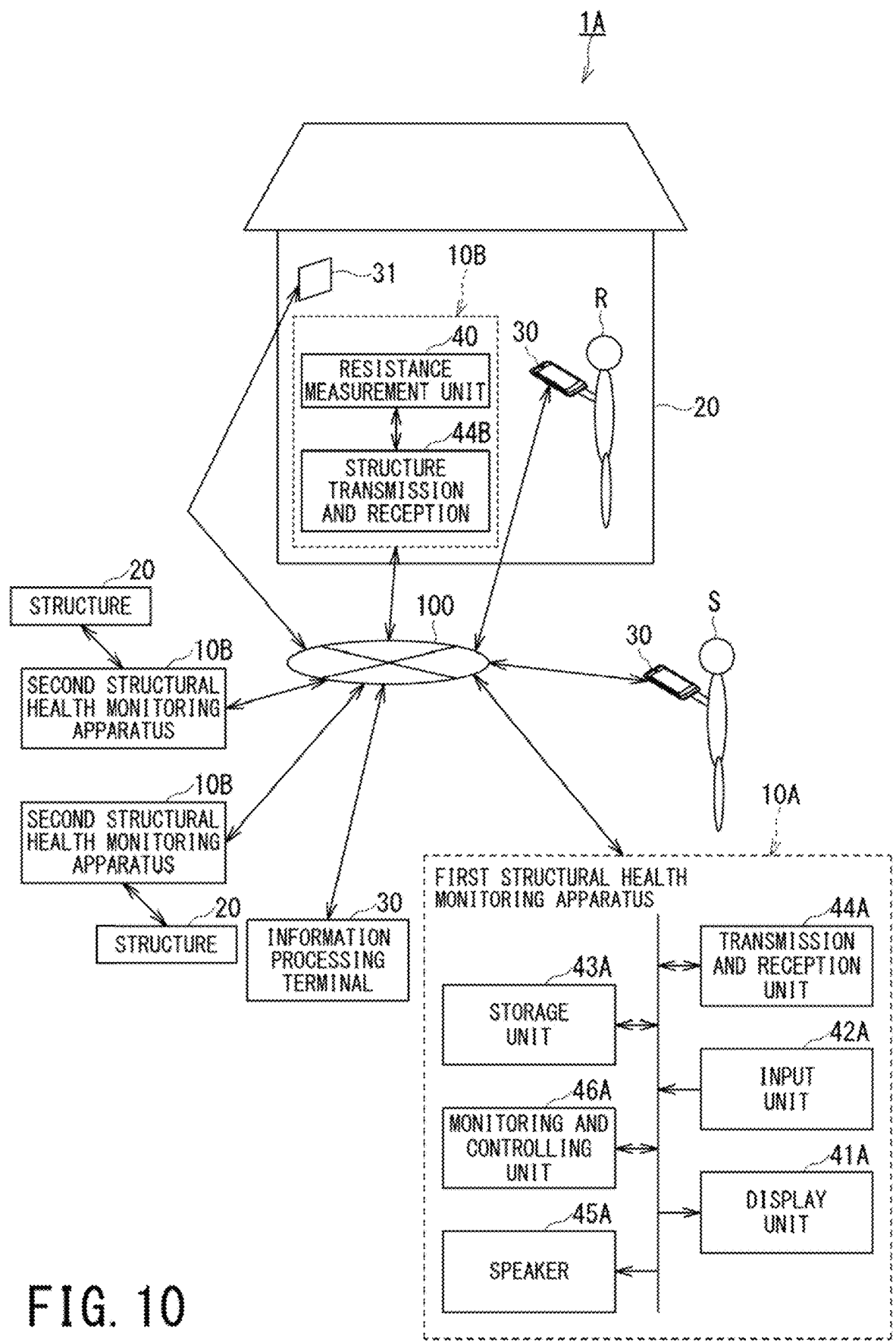
FIG. 10 is a block diagram showing an example of a structural health monitoring system including structural health monitoring apparatuses according to the second embodiment of the present invention.

FIG. 10 is a block diagram showing an example of a structural health monitoring system 1A including structural health monitoring apparatuses 10A and 10B according to the second embodiment of the present invention.

The structural health monitoring apparatuses 10A and 10B and the structural health monitoring system 1A illustrated in the second embodiment are different from the structural health monitoring apparatus 10 and the structural health monitoring system 1 illustrated in the first embodiment in that the functions of the structural health monitoring apparatus 10 according to the first embodiment are divided into a first structural health monitoring apparatus 10A that is part installed on the network 100 and a second structural health monitoring apparatus 10B that is part installed on the structure 20. The other components and actions are substantially not different frost the structural health monitoring system 1 including the structural health monitoring apparatus 10. Therefore, the same reference signs are provided to the same components, and the description will not be repeated.

The second structural health monitoring apparatus 10B is provided in the structure 20 or near the structure 20 and includes the resistance measurement unit 40 and a structure transmission and reception unit 44B. The structure transmission and reception unit 44B transmits the resistance value measurement result of the resistance measurement unit 40 to the first structural health monitoring apparatus 10A through the network 100.

The first structural health monitoring apparatus 10A is provided on the network 100 and includes a display unit 41A, an input unit 42A, a storage unit 43A, a transmission and reception unit 44A, a storage unit 43A, a transmission and controlling unit 46A. The first structural health monitoring apparatus 10A is, for example, a general personal computer, n work station, or a portable information processing terminal such as a tablet terminal. The functions of the units 41A to 43A and 45A are not different from the units 41 to 43 and 45 of the structural health monitoring apparatus 10 according to the first embodiment, and the description will not be repeated.

In addition to the function equivalent to the transmission and reception unit 44 of the structural health monitoring apparatus 10 according to the first embodiment, the transmission and reception unit 44A connects the first structural health monitoring apparatus 10A and the second structural health monitoring apparatus 10B in a manner that data can be transmitted and received.

The structural health monitoring apparatuses 10A and 10B according to the present embodiment also attain advantageous effects similar to the structural health monitoring apparatus 10 according to the first embodiment. Furthermore, according to the structural health monitoring apparatuses 10A and 10B of the present embodiment, one first structural health monitoring apparatus 10A can perform centralized monitoring of the health of a plurality of structures 20 by providing the second structural health monitoring apparatus 10B on each structure 20.

While certain embodiments have been described, these embodiments have been presented by way of example only, and are not intended to limit the scope of the invention. Indeed, the novel embodiments described herein may be embodied in a variety of other forms; furthermore, various omissions, substitutions and changes in the form of the embodiments described herein may be made without departing from the scope of the invention as defined by the appended claims. The accompanying claims and their equivalents are intended to cover such forms or modifications as would fall within the scope of the invention as defined by the appended claims.

Although the present invention is more suitable when the structural materials 21 are materials with a low conductivity such as wood, the present invention can also be applied even when the constituent materials are materials with a high conductivity such as metal and conductive concrete. For example, when the joint portion of the column and the beam is completely separated at only one section due to an earthquake or the like although there is no abnormality in the entire structure in appearance, the structural health monitoring apparatuses 10, 10A and 10B can easily detect the abnormality even if the constituent materials are materials with a high conductivity such as metal and conductive concrete.

What is claimed is:
1. A structural health monitoring system comprising:
    a structure including:
        an assembled body; and
        a plurality of structural materials forming the assembled body and each including joint portions and a shaft portion, wherein at least part of surfaces of the joint portions and at least part of surfaces of the shaft portion are conductive such that, by surfaces of the plurality of structural materials being electrically connected, electrical paths are formed in the assembled body that forms frames of a three- dimensional building assembled by joining the plurality of structural materials through the joint portions; and a structural health monitoring apparatus including:
  a resistance measurement unit configured to measure a resistance value between one terminal and another terminal of a set of two terminals, the set of two terminals being selected from a plurality of terminals provided on the electrical paths, the resistance value being a combined resistance value of all electrical paths from the one terminal to the other terminal of the set of two terminals; and
  an evaluation unit configured to evaluate the health of the structure by using a difference between the resistance value between terminals of the set of two terminals measured by the resistance measurement unit and a reference resistance value between terminals of the set of two terminals, and configured to output evaluation result information.

2. The structural health monitoring system according to claim 1, wherein
among electrical paths between two terminals provided on a same structural material, a shortest electrical path shorter than a predetermined distance is provided with an insulating portion and is electrically opened.

3. The structural health monitoring system according to claim 2, further comprising:
  a switch for short-circuiting the shortest electrical path between two terminals across the insulating portion; and
  a terminal selection unit configured to select a plurality of sets of two terminals from the plurality of terminals, and control each switch to open a switch corresponding to a set to be measured and to short-circuit a switch corresponding to a set not to be measured.

4. The structural health monitoring system according to claim 1, further comprising:
  an evaluation notification unit configured to generate an image according to the evaluation result information of the health of the structure; and
  a transmission and reception unit configured to transmit and receive data to and from a terminal device having at least a display, wherein
  the evaluation notification unit is configured to cause the display of the terminal device through the transmission and reception unit to display the image according to the evaluation result information of the health of the structure.

5. The structural health monitoring system according to claim 2, further comprising:
  an evaluation notification unit configured to generate an image according to the evaluation result information of the health of the structure; and
  a transmission and reception unit configured to transmit and receive data to and from a terminal device having at least a display, wherein
  the evaluation notification unit is configured to cause the display of the terminal device through the transmission and reception unit to display the image according to the evaluation result information of the health of the structure.

6. The structural health monitoring system according to claim 3, further comprising:
  an evaluation notification unit configured to generate an image according to the evaluation result information of the health of the structure; and
  a transmission and reception unit configured to transmit and receive data to and from a terminal device having at least a display, wherein
  the evaluation notification unit is configured to cause the display of the terminal device through the transmission and reception unit to display the image according to the evaluation result information of the health of the structure.

7. The structural health monitoring system according to claim 1, wherein
  the resistance measurement unit is configured to periodically and automatically measure a current resistance value between terminals of the set of two terminals, and
  the evaluation unit is configured to evaluate the health of the structure by using a difference between the current resistance value between terminals of the set of two terminals periodically and automatically measured by the resistance measurement unit and the reference resistance value between terminals of the set of two terminals and to output the evaluation result information.

8. The structural health monitoring system according to claim 2, wherein
  the resistance measurement unit is configured to periodically and automatically measure a current resistance value between terminals of the set of two terminals, and
  the evaluation unit is configured to evaluate the health of the structure by using a difference between the current resistance value between terminals of the set of two terminals periodically and automatically measured by the resistance measurement unit and the reference resistance value between terminals of the set of two terminals and to output the evaluation result information.

9. The structural health monitoring system according to claim 3, wherein
  the resistance measurement unit is configured to periodically and automatically measure a current resistance value between terminals of the set of two terminals, and
  the evaluation unit is configured to evaluate the health of the structure by using a difference between the current resistance value between terminals of the set of two terminals periodically and automatically measured by the resistance measurement unit and the reference resistance value between terminals of the set of two terminals and to output the evaluation result information.

10. The structural health monitoring system according to claim 4, wherein
  the resistance measurement unit is configured to periodically and automatically measure a current resistance value between terminals of the set of two terminals, and
  the evaluation unit is configured to evaluate the health of the structure by using a difference between the current resistance value between terminals of the set of two terminals periodically and automatically measured by the resistance measurement unit and the reference resistance value between terminals of the set of two terminals and to output the evaluation result information.

11. The structural health monitoring system according to claim 5, wherein
  the resistance measurement unit is configured to periodically and automatically measure a current resistance value between terminals of the set of two terminals, and
  the evaluation unit is configured to evaluate the health of the structure by using a difference between the current resistance value between terminals of the set of two terminals periodically and automatically measured by the resistance measurement unit and the reference resistance value between terminals of the set of two terminals and to output the evaluation result information.

12. The structural health monitoring system according to claim 6, wherein
the resistance measurement unit is configured to periodically and automatically measure a current resistance value between terminals of the set of two terminals, and
the evaluation unit is configured to evaluate the health of the structure by using a difference between the current resistance value between terminals of the set of two terminals periodically and automatically measured by the resistance measurement unit and the reference resistance value between terminals of the set of two terminals and to output the evaluation result information.

13. A structural health monitoring method for monitoring health of a structure, the method comprising:
providing the structure including an assembled body and a plurality of structural materials, the plurality of structural materials forming the assembled body and each including joint portions and a shaft portion, wherein at least part of surfaces of the joint portions and at least part of surfaces of the shaft portion are conductive such that, by surfaces of the plurality of structural materials being electrically connected, electrical paths are formed in the assembled body that forms frames of a three-dimensional building assembled by joining the plurality of structural materials through the joint portions;
measuring a resistance value between one terminal and another terminal of a set of two terminals, the set of two terminals being selected from a plurality of terminals provided on the electrical paths, the resistance value being a combined resistance value of all electrical paths from the one terminal to the other terminal of the set of two terminals;
evaluating the health of the structure by using a difference between the resistance value between terminals of the set of two terminals measured by the resistance measurement unit and a reference resistance value between terminals of the set of two terminals; and
outputting evaluation result information.

* * * * *